United States Patent
Hagiya et al.

(10) Patent No.: US 7,579,480 B2
(45) Date of Patent: Aug. 25, 2009

(54) ALKOXY-(TETRAZOL-1-YL) BENZALDEHYDE COMPOUND AND PROCESS FOR PRODUCING THE SAME

(75) Inventors: Kazutake Hagiya, Takasago (JP); Yasuhiro Sato, Takasago (JP)

(73) Assignee: Toyo Kasei Kogyo Company Limited, Osaka (JP)

( * ) Notice: Subject to any disclaimer, the term of this patent is extended or adjusted under 35 U.S.C. 154(b) by 409 days.

(21) Appl. No.: 10/565,801

(22) PCT Filed: Jul. 15, 2004

(86) PCT No.: PCT/JP2004/010437

§ 371 (c)(1),
(2), (4) Date: Jan. 25, 2006

(87) PCT Pub. No.: WO2005/012267

PCT Pub. Date: Feb. 10, 2005

(65) Prior Publication Data

US 2007/0060630 A1    Mar. 15, 2007

(30) Foreign Application Priority Data

Aug. 1, 2003    (JP) ............... 2003-285266

(51) Int. Cl.
 *C07D 257/04* (2006.01)
(52) U.S. Cl. .................................... 548/250
(58) Field of Classification Search ................. 548/250
 See application file for complete search history.

(56) References Cited

U.S. PATENT DOCUMENTS

| | | | | |
|---|---|---|---|---|
| 5,703,240 | A | * 12/1997 | Armour et al. | 546/210 |
| 5,919,803 | A | * 7/1999 | Giblin et al. | 514/329 |
| 2003/0204100 | A1 | 10/2003 | Tamura et al. | 549/462 |

FOREIGN PATENT DOCUMENTS

| | | |
|---|---|---|
| CN | 1135218 A | 11/1996 |
| EP | 0 829 480 A2 | 3/1998 |
| EP | 1 304 328 A1 | 4/2003 |
| WO | 95/08549 A1 | 3/1995 |
| WO | 96/21661 A1 | 7/1996 |
| WO | 96/29326 A1 | 9/1996 |
| WO | 00/18403 A1 | 4/2000 |
| WO | 02/06263 | 1/2002 |

OTHER PUBLICATIONS

Suzuki, Yuji et al., "Formylation of Phenols with Electron-withdrawing Groups in Strong Acids. Synthesis of Substituted Salicylaldehydes", *Chem. Pharm. Bull.*, vol. 31, pp. 1751-1753, 1983.
"Indole-3-Aldehyde", *Org. Synth. Coll.*, vol. 4, pp. 539-542, 1963.
Martínez, Antonio García et al., "A New Procedure for Formylation of Less Active Aromatics", *J. Chem. Soc., Chem. Commun.*, pp. 1571-1572, 1990.
Smith, William E., "Formylation of Aromatic Compounds with Hexamethylenetetramine and Trifluoroacetic Acid", *J. Org. Chem.*, 37, pp. 3972-3973, 1972.
Bergman, Jan et al., "Synthesis of Aromatic Aldehydes via 2-Aryl-N,N'-Diacyl-4-Imidazolines", *Tetrahedron*, vol. 36, pp. 2505-2511, 1980.
Crounse, Nathan N., "The Gattermann-Koch Reaction", *Org. React.*, vol. 5, pp. 290-299, 1960.
Baltazzi, Evan et al., "Recent Advances in the Chemistry of Pyrrole", *Chem. Rev.*, vol. 63, pp. 511-556, 1963.

* cited by examiner

*Primary Examiner*—Golam M. M Shameem
*Assistant Examiner*—Susannah Chung
(74) *Attorney, Agent, or Firm*—Kubovcik & Kubovcik

(57) ABSTRACT

The present invention relates to a process for producing an alkoxy-(tetrazol-1-yl)benzaldehyde compound represented by Formula (2):

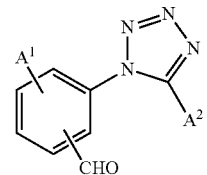

(2)

wherein $A^1$ is an alkoxy group, and $A^2$ is a hydrogen atom, alkyl group or fluorine-substituted alkyl group, the process comprising reacting a 1-(alkoxyphenyl)-1H-tetrazole compound represented by Formula (1):

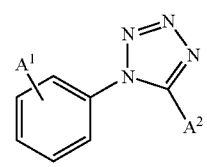

(1)

wherein $A^1$ and $A^2$ are as defined above, with hexamethylenetetramine in a sulfonic acid solvent, followed by hydrolysis. According to the present invention, an alkoxy-(tetrazol-1-yl) benzaldehyde compound can be safely and efficiently produced by formylating a 1-(alkoxyphenyl)-1H-tetrazole compound.

7 Claims, No Drawings

ALKOXY-(TETRAZOL-1-YL) BENZALDEHYDE COMPOUND AND PROCESS FOR PRODUCING THE SAME

This application is a 371 of international application PCT/JP2004/010437, which claims priority based on Japanese patent application No. 2003-285266 filed Aug. 1, 2003, which is incorporated herein by reference.

TECHNICAL FIELD

The present invention relates to novel alkoxy-(tetrazol-1-yl)benzaldehyde compounds and processes for producing the same.

BACKGROUND ART

Use of alkoxy-(tetrazol-1-yl)benzaldehyde compounds as pharmaceutical intermediates has been reported. For example, 2-methoxy-5-(5-methyltetrazol-1-yl)benzaldehyde is known to be of use as an important intermediate for a pharmaceutical that mainly serves as an analgesic or an antiinflammatory agent (EP 0829480A2). Moreover, 2-methoxy-5-(5-trifluoromethyltetrazol-1-yl)benzaldehyde is known to be of use as an important intermediate for a pharmaceutical that mainly serves as an analgesic (WO 96/29326).

Formylation reactions for aromatic compounds have been researched for a long period of time, and there are a variety of reported processes. Typical examples are (1) a process that uses dimethylformamide and phosphorus oxychloride (Org. Synth. Coll. Vol. 4, 1963, p. 539); (2) a process that uses dimethylformamide and trifluoromethanesulfonic anhydride (J. Chem. Soc., Chem. Commun., 1990, p. 1571); (3) a process that uses hexamethylenetetramine and trifluoroacetic acid (J. Org. Chem., vol. 37, 1972, p. 3972); (4) a process that uses imidazole and trifluoroacetic anhydride (Tetrahedron, vol. 36, 1980, p. 2505); (5) a process that uses carbon monoxide, hydrochloric acid and aluminium(III) chloride (Org. React., vol. 5, 1960, p. 290); and (6) a process that uses zinc(II) cyanide, hydrochloric acid and aluminium(III) chloride (Chem. Rev., vol. 63, 1963, p. 526).

However, when 1-(alkoxyphenyl)-1H-tetrazole compounds are subjected to formylation reactions according to processes (1) to (4) above, the reactions hardly progress. Processes (5) and (6) may be hazardous when used for commercial production because in process (5) toxic carbon monoxide is used, and in process (6) hydrogen cyanide is generated in the reaction system.

Therefore, formylation reactions for 1-(alkoxyphenyl)-1H-tetrazole compounds do not progress or are hazardous when prior-art processes are used. Prior-art processes are thus not industrially advantageous.

DISCLOSURE OF THE INVENTION

An object of the present invention is to provide a process for safely and efficiently producing an alkoxy-(tetrazol-1-yl) benzaldehyde compound by formylating a 1-(alkoxyphenyl)-1H-tetrazole compound.

Other objects and characteristics of the present invention will become evident by the disclosure provided hereinbelow.

The inventors conducted extensive research to achieve the object described above, and found that alkoxy-(tetrazol-1-yl) benzaldehyde compounds can be safely and efficiently produced by subjecting 1-(alkoxyphenyl)-1H-tetrazole compounds to a reaction with hexamethylenetetramine in a sulfonic acid solvent and then to hydrolysis, and the inventors accomplished the present invention.

In particular, the present invention provides alkoxy-(tetrazol-1-yl)benzaldehyde compounds and processes for producing the same as described below.

1. A process for producing an alkoxy-(tetrazol-1-yl)benzaldehyde compound represented by Formula (2):

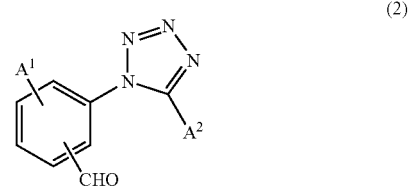

wherein $A^1$ is an alkoxy group, and $A^2$ is a hydrogen atom, alkyl group or fluorine-substituted alkyl group, the process comprising reacting a 1-(alkoxyphenyl)-1H-tetrazole compound represented by Formula (1):

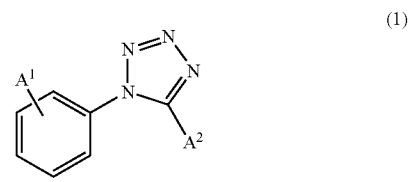

wherein $A^1$ and $A^2$ are as defined above, with hexamethylenetetramine in a sulfonic acid solvent, followed by hydrolysis.

2. The process according to Item 1, wherein the sulfonic acid solvent is a mixed solvent of methanesulfonic acid and trifluoromethanesulfonic acid.

3. The process according to Item 1 or 2, wherein hexamethylenetetramine is used in an amount of 1.0 to 3.0 mol per mol of the 1-(alkoxyphenyl)-1H-tetrazole compound.

4. The process according to any one of Items 1 to 3, wherein $A^1$ is a methoxy group, and $A^2$ is a hydrogen atom, methyl group, ethyl group or trifluoromethyl group.

5. A process for producing a 4-alkoxy-3-(tetrazol-1-yl)benzaldehyde compound represented by Formula (4):

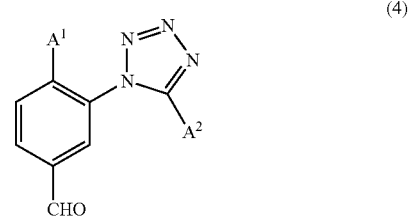

wherein $A^1$ is an alkoxy group, and $A^2$ is a hydrogen atom, alkyl group or fluorine-substituted alkyl group, the process comprising reacting a 1-(2-alkoxyphenyl)-1H-tetrazole compound represented by Formula (3):

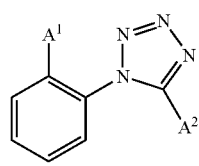
(3)

wherein $A^1$ and $A^2$ are as defined above, with hexamethylenetetramine in a sulfonic acid solvent, followed by hydrolysis.

6. A process for producing a 2-alkoxy-4-(tetrazol-1-yl)benzaldehyde compound represented by Formula (6):

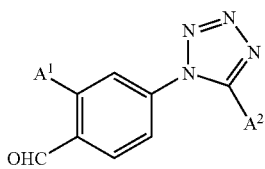
(6)

wherein $A^1$ is an alkoxy group, and $A^2$ is a hydrogen atom, alkyl group or fluorine-substituted alkyl group, the process comprising reacting a 1-(3-alkoxyphenyl)-1H-tetrazole compound represented by Formula (5):

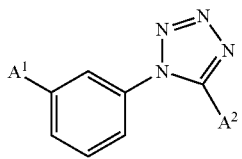
(5)

wherein $A^1$ and $A^2$ are as defined above, with hexamethylenetetramine in a sulfonic acid solvent, followed by hydrolysis.

7. A process for producing a 2-alkoxy-5-(tetrazol-1-yl)benzaldehyde compound represented by Formula (8):

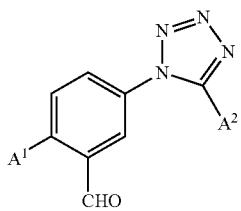
(8)

wherein $A^1$ is an alkoxy group, and $A^2$ is a hydrogen atom, alkyl group or fluorine-substituted alkyl group, the process comprising reacting a 1-(4-alkoxyphenyl)-1H-tetrazole compound represented by Formula (7):

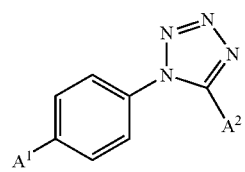
(7)

wherein $A^1$ and $A^2$ are as defined above, with hexamethylenetetramine in a sulfonic acid solvent, followed by hydrolysis.

8. An alkoxy-(tetrazol-1-yl)benzaldehyde compound represented by Formula (2):

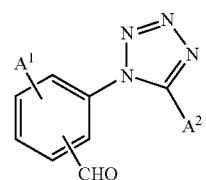
(2)

wherein $A^1$ is an alkoxy group, and $A^2$ is a hydrogen atom, alkyl group or fluorine-substituted alkyl group, with the proviso that the compound is not a 2-alkoxy-5-(tetrazol-1-yl)benzaldehyde compound represented by Formula (8):

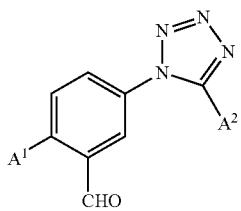
(8)

wherein $A^1$ and $A^2$ are as defined above.

9. The alkoxy-(tetrazol-1-yl)benzaldehyde compound according to Item 8, wherein the aldehyde group is in an ortho or para position relative to $A^1$.

10. A 4-alkoxy-3-(tetrazol-1-yl)benzaldehyde compound represented by Formula (4):

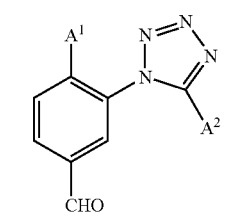
(4)

wherein $A^1$ is an alkoxy group, and $A^2$ is a hydrogen atom, alkyl group or fluorine-substituted alkyl group.

11. A 2-alkoxy-4-(tetrazol-1-yl)benzaldehyde compound represented by Formula (6):

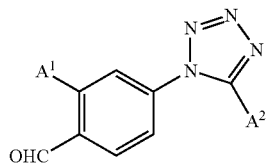

(6)

wherein $A^1$ is an alkoxy group, and $A^2$ is a hydrogen atom, alkyl group or fluorine-substituted alkyl group.

The present invention is described below in detail.

$A^1$ and $A^2$ in Formulas (1) to (8) presented above are described first.

The alkyl moiety of an alkoxy group represented by $A^1$ may be linear or branched. When branched, the number and position(s) of branch(es) are not limited. For the reaction to progress smoothly, the alkyl moiety preferably has 1 to 10 carbon atoms, and more preferably 1 to 4 carbon atoms. Preferable and specific examples of alkoxy groups are methoxy, ethoxy, n-propoxy, isopropoxy, butoxy, but-2-oxy, 2-methylprop-1-oxy, 2-methylprop-2-oxy, and like groups.

An alkyl group represented by $A^2$ may be linear or branched. When branched, the number and position(s) of branch(es) are not limited. For the reaction to progress smoothly, the alkyl group preferably has 1 to 10 carbon atoms, and more preferably 1 to 3 carbon atoms. Preferable and specific examples are methyl, ethyl, n-propyl, isopropyl, and like groups.

An alkyl group represented by $A^2$ in which hydrogen atom(s) are substituted by fluorine atom(s) is preferably, in terms of availability, a $C_{1-4}$ linear alkyl group in which all hydrogen atoms are substituted by fluorine atoms, and more preferably a $C_{1-2}$ alkyl group in which all hydrogen atoms are substituted by fluorine atoms. Preferable and specific examples are trifluoromethyl, pentafluoroethyl, and like groups.

In the present invention, a methoxy group is particularly preferable for $A^1$. A hydrogen atom or a methyl, ethyl or trifluoromethyl group is particularly preferable for $A^2$.

In the present invention, examples of 1-(alkoxyphenyl)-1H-tetrazole compounds represented by Formula (1) are 1-(2-alkoxyphenyl)-1H-tetrazole compounds represented by Formula (3), 1-(3-alkoxyphenyl)-1H-tetrazole compounds represented by Formula (5), 1-(4-alkoxyphenyl)-1H-tetrazole compounds represented by Formula (7), etc.

1-(2-Alkoxyphenyl)-1H-tetrazole compounds represented by Formula (3) may be prepared according to any process. Specific examples are 1-(2-methoxyphenyl)-1H-tetrazole, 1-(2-ethoxyphenyl)-1H-tetrazole, 1-(2-propoxyphenyl)-1H-tetrazole, 1-(2-isopropoxyphenyl)-1H-tetrazole, 1-(2-butoxyphenyl)-1H-tetrazole, 1-[2-(but-2-oxy)phenyl]-1H-tetrazole, 1-[2-(2-methylprop-1-oxy)phenyl]-1H-tetrazole, 1-[2-(2-methylprop-2-oxy)phenyl]-1H-tetrazole, 1-(2-methoxyphenyl)-5-methyl-1H-tetrazole, 1-(2-ethoxyphenyl)-5-methyl-1H-tetrazole, 1-(2-propoxyphenyl)-5-methyl-1H-tetrazole, 1-(2-isopropoxyphenyl)-5-methyl-1H-tetrazole, 1-(2-butoxyphenyl)-5-methyl-1H-tetrazole, 1-[2-(but-2-oxy)phenyl]-5-methyl-1H-tetrazole, 1-[2-(2-methylprop-1-oxy)phenyl]-5-methyl-1H-tetrazole, 1-[2-(2-methylprop-2-oxy)phenyl]-5-methyl-1H-tetrazole, 1-(2-methoxyphenyl)-5-ethyl-1H-tetrazole, 1-(2-ethoxyphenyl)-5-ethyl-1H-tetrazole, 1-(2-propoxyphenyl)-5-ethyl-1H-tetrazole, 1-(2-isopropoxyphenyl)-5-ethyl-1H-tetrazole, 1-(2-butoxyphenyl)-5-ethyl-1H-tetrazole, 1-[2-(but-2-oxy)phenyl]-5-ethyl-1H-tetrazole, 1-[2-(2-methylprop-1-oxy)phenyl]-5-ethyl-1H-tetrazole, 1-[2-(2-methylprop-2-oxy)phenyl]-5-ethyl-1H-tetrazole, 1-(2-methoxyphenyl)-5-propyl-1H-tetrazole, 1-(2-ethoxyphenyl)-5-propyl-1H-tetrazole, 1-(2-propoxyphenyl)-5-propyl-1H-tetrazole, 1-(2-isopropoxyphenyl)-5-propyl-1H-tetrazole, 1-(2-butoxyphenyl)-5-propyl-1H-tetrazole, 1-[2-(but-2-oxy)phenyl]-5-propyl-1H-tetrazole, 1-[2-(2-methylprop-1-oxy)phenyl]-5-propyl-1H-tetrazole, 1-[2-(2-methylprop-2-oxy)phenyl]-5-propyl-1H-tetrazole, 1-(2-methoxyphenyl)-5-isopropyl-1H-tetrazole, 1-(2-ethoxyphenyl)-5-isopropyl-1H-tetrazole, 1-(2-propoxyphenyl)-5-isopropyl-1H-tetrazole, 1-(2-isopropoxyphenyl)-5-isopropyl-1H-tetrazole, 1-(2-butoxyphenyl)-5-isopropyl-1H-tetrazole, 1-[2-(but-2-oxy)phenyl]-5-isopropyl-1H-tetrazole, 1-[2-(2-methylprop-1-oxy)phenyl]-5-isopropyl-1H-tetrazole, 1-[2-(2-methylprop-2-oxy)phenyl]-5-isopropyl-1H-tetrazole, 1-(2-methoxyphenyl)-5-trifluoromethyl-1H-tetrazole, 1-(2-ethoxyphenyl)-5-trifluoromethyl-1H-tetrazole, 1-(2-propoxyphenyl)-5-trifluoromethyl-1H-tetrazole, 1-(2-isopropoxyphenyl)-5-trifluoromethyl-1H-tetrazole, 1-(2-butoxyphenyl)-5-trifluoromethyl-1H-tetrazole, 1-[2-(but-2-oxy)phenyl]-5-trifluoromethyl-1H-tetrazole, 1-[2-(2-methylprop-1-oxy)phenyl]-5-trifluoromethyl-1H-tetrazole, 1-[2-(2-methylprop-2-oxy)phenyl]-5-trifluoromethyl-1H-tetrazole, 1-(2-methoxyphenyl)-5-pentafluoroethyl-1H-tetrazole, 1-(2-ethoxyphenyl)-5-pentafluoroethyl-1H-tetrazole, 1-(2-propoxyphenyl)-5-pentafluoroethyl-1H-tetrazole, 1-(2-isopropoxyphenyl)-5-pentafluoroethyl-1H-tetrazole, 1-(2-butoxyphenyl)-5-pentafluoroethyl-1H-tetrazole, 1-[2-(but-2-oxy)phenyl]-5-pentafluoroethyl-1H-tetrazole, 1-[2-(2-methylprop-1-oxy)phenyl]-5-pentafluoroethyl-1H-tetrazole, and 1-[2-(2-methylprop-2-oxy)phenyl]-5-pentafluoroethyl-1H-tetrazole. Among these examples, 1-(2-methoxyphenyl)-1H-tetrazole, 1-(2-methoxyphenyl)-5-methyl-1H-tetrazole, 1-(2-methoxyphenyl)-5-ethyl-1H-tetrazole, and 1-(2-methoxyphenyl)-5-trifluoromethyl-1H-tetrazole are particularly preferable.

1-(3-Alkoxyphenyl)-1H-tetrazole compounds represented by Formula (5) may be prepared according to any process. Specific examples are 1-(3-methoxyphenyl)-1H-tetrazole, 1-(3-ethoxyphenyl)-1H-tetrazole, 1-(3-propoxyphenyl)-1H-tetrazole, 1-(3-isopropoxyphenyl)-1H-tetrazole, 1-(3-butoxyphenyl)-1H-tetrazole, 1-[3-(but-2-oxy)phenyl]-1H-tetrazole, 1-[3-(2-methylprop-1-oxy)phenyl]-1H-tetrazole, 1-[3-(2-methylprop-2-oxy)phenyl]-1H-tetrazole, 1-(3-methoxyphenyl)-5-methyl-1H-tetrazole, 1-(3-ethoxyphenyl)-5-methyl-1H-tetrazole, 1-(3-propoxyphenyl)-5-methyl-1H-tetrazole, 1-(3-isopropoxyphenyl)-5-methyl-1H-tetrazole, 1-(3-butoxyphenyl)-5-methyl-1H-tetrazole, 1-[3-(but-2-oxy)phenyl]-5-methyl-1H-tetrazole, 1-[3-(2-methylprop-1-oxy)phenyl]-5-methyl-1H-tetrazole, 1-[3-(2-methylprop-2-oxy)phenyl]-5-methyl-1H-tetrazole, 1-(3-methoxyphenyl)-5-ethyl-1H-tetrazole, 1-(3-ethoxyphenyl)-5-ethyl-1H-tetrazole, 1-(3-propoxyphenyl)-5-ethyl-1H-tetrazole, 1-(3-isopropoxyphenyl)-5-ethyl-1H-tetrazole, 1-(3-butoxyphenyl)-5-ethyl-1H-tetrazole, 1-[3-(but-2-oxy)phenyl]-5-ethyl-1H-tetrazole, 1-[3-(2-methylprop-1-oxy)phenyl]-5-ethyl-1H-tetrazole, 1-[3-(2-methylprop-2-oxy)phenyl]-5-ethyl-1H-tetrazole, 1-(3-methoxyphenyl)-5-propyl-1H-tetrazole, 1-(3-ethoxyphenyl)-5-propyl-1H-tetrazole, 1-(3-propoxyphenyl)-5-propyl-1H-tetrazole, 1-(3-isopropoxyphenyl)-5-propyl-1H-tetrazole, 1-(3- butoxyphenyl)-5-propyl-1H-tetrazole, 1-[3-(but-2-oxy)phenyl]-5-propyl-1H-tetrazole, 1-[3-(2-methylprop-1-oxy)phenyl]-5-propyl-1H-tetrazole, 1-[3-(2-methylprop-2-oxy)phenyl]-5-propyl-1H-tetrazole, 1-(3-methoxyphenyl)-5-isopropyl-1H-tetrazole, 1-(3-ethoxyphenyl)-5-isopropyl-1H-tetrazole, 1-(3-propoxyphenyl)-5-isopropyl-1H-tetrazole, 1-(3-isopropoxyphenyl)-5-isopropyl-1H-tetrazole, 1-(3-butoxyphenyl)-5-isopropyl-1H-tetrazole, 1-[3-(but-2-oxy)phenyl]-5-isopropyl-1H-tetrazole, 1-[3-(2-methylprop-1-oxy)phenyl]-5-isopropyl-1H-tetrazole, 1-[3-(2-methylprop-2-oxy)phenyl]-5-isopropyl-1H-tetrazole, 1-(3-methoxyphenyl)-5-trifluoromethyl-1H-tetrazole, 1-(3-ethoxyphenyl)-5-trifluoromethyl-1H-tetrazole, 1-(3-propoxyphenyl)-5-trifluoromethyl-1H-tetrazole, 1-(3-isopropoxyphenyl)-5-trifluoromethyl-1H-tetrazole, 1-(3-butoxyphenyl)-5-trifluoromethyl-1H-tetrazole, 1-[3-(but-2-oxy)phenyl]-5-trifluoromethyl-1H-tetrazole, 1-[3-(2-methylprop-1-oxy)phenyl]-5-trifluoromethyl-1H-tetrazole, 1-[3-(2-methylprop-2-oxy)phenyl]-5-trifluoromethyl-1H-tetrazole, 1-(3-methoxyphenyl)-5-pentafluoroethyl-1H-tetrazole, 1-(3-ethoxyphenyl)-5-pentafluoroethyl-1H-tetrazole, 1-(3-propoxyphenyl)-5-pentafluoroethyl-1H-tetrazole, 1-(3-isopropoxyphenyl)-5-pentafluoroethyl-1H-tetrazole, 1-(3-butoxyphenyl)-5-pentafluoroethyl-1H-tetrazole, 1-[3-(but-2-oxy)phenyl]-5-pentafluoroethyl-1H-tetrazole, 1-[3-(2-methylprop-1-oxy)phenyl]-5-pentafluoroethyl-1H-tetrazole, and 1-[3-(2-methylprop-2-oxy)phenyl]-5-pentafluoroethyl-1H-tetrazole. Among these examples, 1-(3-methoxyphenyl)-1H-tetrazole, 1-(3-methoxyphenyl)-5-methyl-1H-tetrazole, 1-(3-methoxyphenyl)-5-ethyl-1H-tetrazole, and 1-(3-methoxyphenyl)-5-trifluoromethyl-1H-tetrazole are particularly preferable.

1-(4-Alkoxyphenyl)-1H-tetrazole compounds represented by Formula (7) may be prepared according to any process. Specific examples are 1-(4-methoxyphenyl)-1H-tetrazole, 1-(4-ethoxyphenyl)-1H-tetrazole, 1-(4-propoxyphenyl)-1H-tetrazole, 1-(4-isopropoxyphenyl)-1H-tetrazole, 1-(4-butoxyphenyl)-1H-tetrazole, 1-[4-(but-2-oxy)phenyl]-1H-tetrazole, 1-[4-(2-methylprop-1-oxy)phenyl]-1H-tetrazole, 1-[4-(2-methylprop-2-oxy)phenyl]-1H-tetrazole, 1-(4-methoxyphenyl)-5-methyl-1H-tetrazole, 1-(4-ethoxyphenyl)-5-methyl-1H-tetrazole, 1-(4-propoxyphenyl)-5-methyl-1H-tetrazole, 1-(4-isopropoxyphenyl)-5-methyl-1H-tetrazole, 1-(4-butoxyphenyl)-5-methyl-1H-tetrazole, 1-[4-(but-2-oxy)phenyl]-5-methyl-1H-tetrazole, 1-[4-(2-methylprop-1-oxy)phenyl]-5-methyl-1H-tetrazole, 1-[4-(2-methylprop-2-oxy)phenyl]-5-methyl-1H-tetrazole, 1-(4-methoxyphenyl)-5-ethyl-1H-tetrazole, 1-(4-ethoxyphenyl)-5-ethyl-1H-tetrazole, 1-(4-propoxyphenyl)-5-ethyl-1H-tetrazole, 1-(4-isopropoxyphenyl)-5-ethyl-1H-tetrazole, 1-(4-butoxyphenyl)-5-ethyl-1H-tetrazole, 1-[4-(but-2-oxy)phenyl]-5-ethyl-1H-tetrazole, 1-[4-(2-methylprop-1-oxy)phenyl]-5-ethyl-1H-tetrazole, 1-[4-(2-methylprop-2-oxy)phenyl]-5-ethyl-1H-tetrazole, 1-(4-methoxyphenyl)-5-propyl-1H-tetrazole, 1-(4-ethoxyphenyl)-5-propyl-1H-tetrazole, 1-(4-propoxyphenyl)-5-propyl-1H-tetrazole, 1-(4-isopropoxyphenyl)-5-propyl-1H-tetrazole, 1-(4-butoxyphenyl)-5-propyl-1H-tetrazole, 1-[4-(but-2-oxy)phenyl]-5-propyl-1H-tetrazole, 1-[4-(2-methylprop-1-oxy)phenyl]-5-propyl-1H-tetrazole, 1-[4-(2-methylprop-2-oxy)phenyl]-5-propyl-1H-tetrazole, 1-(4-methoxyphenyl)-5-isopropyl-1H-tetrazole, 1-(4-ethoxyphenyl)-5-isopropyl-1H-tetrazole, 1-(4-propoxyphenyl)-5-isopropyl-1H-tetrazole, 1-(4-isopropoxyphenyl)-5-isopropyl-1H-tetrazole, 1-(4-butoxyphenyl)-5-isopropyl-1H-tetrazole, 1-[4-(but-2-oxy)phenyl]-5-isopropyl-1H-tetrazole, 1-[4-(2-methylprop-1-oxy)phenyl]-5-isopropyl-1H-tetrazole, 1-[4-(2-methylprop-2-oxy)phenyl]-5-isopropyl-1H-tetrazole, 1-(4-methoxyphenyl)-5-trifluoromethyl-1H-tetrazole, 1-(4-ethoxyphenyl)-5-trifluoromethyl-1H-tetrazole, 1-(4-propoxyphenyl)-5-trifluoromethyl-1H-tetrazole, 1-(4-isopropoxyphenyl)-5-trifluoromethyl-1H-tetrazole, 1-(4-butoxyphenyl)-5-trifluoromethyl-1H-tetrazole, 1-[4-(but-2-oxy)phenyl]-5-trifluoromethyl-1H-tetrazole, 1-[4-(2-methylprop-1-oxy)phenyl]-5-trifluoromethyl-1H-tetrazole, 1-[4-(2-methylprop-2-oxy)phenyl]-5-trifluoromethyl-1H-tetrazole, 1-(4-methoxyphenyl)-5-pentafluoroethyl-1H-tetrazole, 1-(4-ethoxyphenyl)-5-pentafluoroethyl-1H-tetrazole, 1-(4-propoxyphenyl)-5-pentafluoroethyl-1H-tetrazole, 1-(4-isopropoxyphenyl)-5-pentafluoroethyl-1H-tetrazole, 1-(4-butoxyphenyl)-5-pentafluoroethyl-1H-tetrazole, 1-[4-(but-2-oxy)phenyl]-5-pentafluoroethyl-1H-tetrazole, 1-[4-(2-methylprop-1-oxy)phenyl]-5-pentafluoroethyl-1H-tetrazole, and 1-[4-(2-methylprop-2-oxy)phenyl]-5-pentafluoroethyl-1H-tetrazole. Among these examples, 1-(4-methoxyphenyl)-1H-tetrazole, 1-(4-methoxyphenyl)-5-methyl-1H-tetrazole, 1-(4-methoxyphenyl)-5-ethyl-1H-tetrazole, and 1-(4-methoxyphenyl)-5-trifluoromethyl-1H-tetrazole are particularly preferable.

In the process for producing an alkoxy-(tetrazol-1-yl)benzaldehyde compound of the present invention, the amount of hexamethylenetetramine is preferably 1.0 to 3.0 mol, and more preferably 1.2 to 2.0 mol, per mol of 1-(alkoxyphenyl)-1H-tetrazole compound of Formula (1).

Sulfonic acid solvents usable in the present invention are not limited insofar as water is not contained therein. Preferable sulfonic acid solvents are those that can dissolve 1-(alkoxyphenyl)-1H-tetrazole compounds of Formula (1). Specific examples are methanesulfonic acid, ethanesulfonic acid, trifluoromethanesulfonic acid, pentafluoroethanesulfonic acid, etc. Such solvents may be used either singly as homosolvents or in suitable combinations as mixed solvents. Among such sulfonic acid solvents, particularly preferable is a mixed solvent in which methanesulfonic acid:trifluoromethanesulfonic acid=1:0.6-1.5 (volume ratio). The amount of sulfonic acid solvent is preferably 1 to 15 ml, and more preferably 5 to 10 ml, per gram of 1-(alkoxyphenyl)-1H-tetrazole compound of Formula (1).

The reaction of a 1-(alkoxyphenyl)-1H-tetrazole compound of Formula (1) with hexamethylenetetramine is carried out in a sulfonic acid solvent with heating. Excessively low reaction temperatures slow the reaction, and excessively high reaction temperatures result in the generation of large amounts of by-products. Therefore, the reaction temperature is preferably about 50 to about 150° C., and more preferably about 80 to about 100° C. The reaction time is about 1 to about 8 hours, and more preferably about 2 to about 5 hours.

After reaction, the reaction system is cooled to room temperature, and then either water is introduced into the reaction system or the reaction solution is introduced into water for hydrolysis. The amount of water is preferably 1 to 15 ml, and more preferably 5 to 15 ml, per gram of 1-(alkoxyphenyl)-1H-tetrazole compound of Formula (1). The temperature for hydrolysis is preferably about 0 to about 30° C., and more preferably about 0 to about 15° C. The hydrolysis time is preferably about 15 minutes to about 2 hours, and more preferably about 30 minutes to about 1 hour.

Thereafter, extraction, separation, drying, solvent evaporation or like ordinary procedures are performed to obtain a crude product. Purification by crystallization, recrystallization, column chromatography, or the like can then be performed to obtain the alkoxy-(tetrazol-1-yl)benzaldehyde compound represented by Formula (2).

In the present invention, examples of alkoxy-(tetrazol-1-yl)benzaldehyde compounds represented by Formula (2) include 4-alkoxy-3-(tetrazol-1-yl)benzaldehyde compounds represented by Formula (4), 2-alkoxy-4-(tetrazol-1-yl)benzaldehyde compounds represented by Formula (6), 2-alkoxy-5-(tetrazol-1-yl)benzaldehyde compounds represented by Formula (8), etc. In alkoxy-(tetrazol-1-yl)benzaldehyde compounds represented by Formula (2), an aldehyde group is present preferably in an ortho or para position relative to $A^1$.

According to the present invention, alkoxy-(tetrazol-1-yl)benzaldehyde compounds can be safely and efficiently produced by formylating 1-(alkoxyphenyl)-1H-tetrazole compounds.

BEST MODE FOR CARRYING OUT THE INVENTION

Examples are given below to illustrate the invention in more detail, but the scope of the invention is not limited to these examples.

Example 1

4-Methoxy-3-(tetrazol-1-yl)benzaldehyde

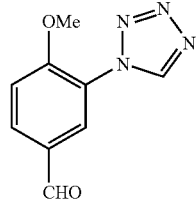

Three grams of 1-(2-methoxyphenyl)-1H-tetrazole (17.0 mmol), 15 ml of methanesulfonic acid, 15 ml of trifluoromethanesulfonic acid, and 4.77 g of hexamethylenetetramine (34.0 mmol) were introduced into a 100 ml flask, and heated to 100° C. for reaction for 3 hours. After reaction, the reaction solution was cooled to room temperature, introduced into 30 ml of water cooled in an ice bath, and stirred at 5° C. for 30 minutes. The reaction solution was then extracted with dichloromethane (60 ml×3), and the organic phase thus obtained was washed with 10% aqueous sodium hydroxide solution (90 ml×1) and water (90 ml×1), and dried over anhydrous magnesium sulfate for 1 hour. After drying, filtration and solvent evaporation were performed, and the crude product thus obtained was subjected to crystallization in a mixed solvent containing 6 ml of dichloromethane and 9 ml of isopropyl alcohol while cooling in an ice bath. After filtration and drying, 0.97 g of 4-methoxy-3-(tetrazol-1-yl)benzaldehyde was obtained as a white solid (yield: 27.9%).

Melting point: 156.8 to 158.7° C.

IR (KBr, cm$^{-1}$): 3155, 1688, 1607, 1516, 1468, 1439, 1292, 1258, 1221, 1180, 1153, 1088, 1009, 901, 820, 671, 662, 640

$^1$H-NMR (CDCl$_3$): δ 9.98 (s, 1H), 9.17 (s, 1H), 8.36 (d, J=2.0 Hz, 1H), 8.04 (dd, J=8.6 Hz, 2.0 Hz, 1H), 7.27 (d, J=8.6 Hz, 1H), 4.06 (s, 3H)

$^{13}$C-NMR (CDCl$_3$): δ 188.91, 154.89, 142.78, 132.13, 130.32, 126.38, 123.62, 112.64, 56.97

Elemental analysis:
Value calculated for C$_9$H$_8$N$_4$O$_2$: C, 52.94%; H, 3.95%; N, 27.44%; Value found: C, 52.92%; H, 3.57%; N, 26.91%.

Example 2

4-Methoxy-3-(5-methyltetrazol-1-yl)benzaldehyde

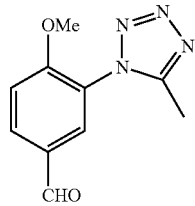

100 mg of 1-(2-methoxyphenyl)-5-methyl-1H-tetrazole (0.526 mmol), 0.5 ml of methanesulfonic acid, 0.5 ml of trifluoromethanesulfonic acid, and 111 mg of hexamethylenetetramine (0.789 mmol) were introduced into a 10 ml flask, and heated to 100° C. for reaction for 3 hours. After reaction, the reaction solution was cooled to room temperature, introduced into 1 ml of water cooled in an ice bath, and stirred at 5° C. for 30 minutes. The reaction solution was then extracted with dichloromethane (5 ml×3), and the organic phase thus obtained was washed with 10% aqueous sodium hydroxide solution (10 ml×1) and water (10 ml×1), and dried over anhydrous magnesium sulfate for 1 hour. After drying, filtration and solvent evaporation were performed, and the crude product thus obtained was purified by column chromatography (silica gel, dichloromethane), resulting in 68 mg of 4-methoxy-3-(5-methyltetrazol-1-yl)benzaldehyde as a white solid (yield: 59.3%). Melting point: 156.9 to 157.4° C.

IR (KBr, cm$^{-1}$): 2998, 2805, 1689, 1605, 1508, 1290, 1271, 1252, 1180, 1011, 824

$^1$H-NMR (CDCl$_3$): δ 9.94 (s, 1H), 8.10 (dd, J=8.5 Hz, 2.0 Hz, 1H), 7.91 (d, J=2.0 Hz, 1H), 7.25 (d, J=8.5 Hz, 1H), 3.93 (s, 3H), 2.45 (s, 3H)

$^{13}$C-NMR (CDCl$_3$): δ 188.90, 158.16, 153.15, 134.09, 130.04, 129.42, 123.11, 112.56, 56.67, 9.12

Elemental analysis:
Value calculated for C$_{10}$H$_{10}$N$_4$O$_2$: C, 55.04%; H, 4.62%; N, 25.68%; Value found: C, 55.11%; H, 4.45%; N, 25.41%.

Example 3

4-Methoxy-3-(5-trifluoromethyltetrazol-1-yl)benzaldehyde

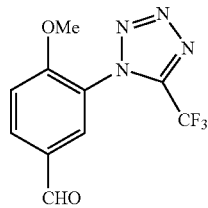

Three grams of 1-(2-methoxyphenyl)-5-trifluoromethyl-1H-tetrazole (12.3 mmol), 15 ml of methanesulfonic acid, 15 ml of trifluoromethanesulfonic acid, and 3.45 g of hexamethylenetetramine (24.6 mmol) were introduced into a 100 ml flask, and heated to 100° C. for reaction for 3 hours. After reaction, the reaction solution was cooled to room temperature, introduced into 30 ml of water cooled in an ice bath, and stirred at 5° C. for 30 minutes. The reaction solution was then extracted with dichloromethane (60 ml×3), and the organic phase thus obtained was washed with 10% aqueous sodium hydroxide solution (90 ml×1) and water (90 ml×1), and dried over anhydrous magnesium sulfate for 1 hour. After drying, filtration and solvent evaporation were performed, and the crude product thus obtained was subjected to crystallization in a mixed solvent containing 9 ml of isopropyl alcohol and 9 ml of diisopropyl ether while cooling in an ice bath. After filtration and drying, 2.14 g of 4-methoxy-3-(5-trifluoromethyltetrazol-1-yl)benzaldehyde was obtained as a white solid (yield: 62.2%). Melting point: 78.5 to 79.6° C.

IR (KBr, cm$^{-1}$): 1699, 1611, 1530, 1512, 1460, 1304, 1287, 1256, 1177, 1144, 1105, 1045, 1030, 1011, 901, 826, 756, 679, 638

$^1$H-NMR (CDCl$_3$): δ 9.95 (s, 1H), 8.15 (dd, J=8.5 Hz, 2.0 Hz, 1H), 7.94 (s, 1H), 7.26 (d, J=8.5 Hz, 1H), 3.92 (s, 3H)

$^{13}$C-NMR (CDCl$_3$): δ 188.43, 158.08, 147.72, 147.30, 146.88, 146.46, 135.11, 129.66, 128.54, 122.05, 121.61, 118.90, 116.21, 113.50, 112.48, 56.70

Elemental analysis:
Value calculated for C$_{10}$H$_7$F$_3$N$_4$O$_2$: C, 44.13%; H, 2.59%; N, 20.58%; Value found: C, 43.82%; H, 2.56%; N, 20.41%.

Example 4

2-Methoxy-4-(5-methyltetrazol-1-yl)benzaldehyde

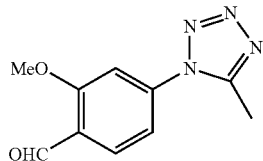

One gram of 1-(3-methoxyphenyl)-5-methyl-1H-tetrazole (5.26 mmol), 5 ml of methanesulfonic acid, 5 ml of trifluoromethanesulfonic acid, and 1.12 g of hexamethylenetetramine (7.89 mmol) were introduced into a 20 ml flask, and heated to 100° C. for reaction for 3.5 hours. After reaction, the reaction solution was cooled to room temperature, introduced into 15 ml of water cooled in an ice bath, and stirred at 5° C. for 30 minutes. The reaction solution was then extracted with dichloromethane (20 ml×3), and the organic phase thus obtained was washed with 10% aqueous sodium hydroxide solution (20 ml×1) and water (20 ml×1), and dried over anhydrous magnesium sulfate for 1 hour. After drying, filtration and solvent evaporation were performed, and the crude product thus obtained was recrystallized in a mixed solvent containing 0.5 ml of dichloromethane and 1 ml of toluene. After filtration and drying, 171 mg of 2-methoxy-4-(5-methyltetrazol-1-yl)benzaldehyde was obtained as a white solid (yield: 14.9%). Melting point: 131.7 to 132.0° C.

IR (KBr, cm$^{-1}$): 3072, 2876, 1684, 1609, 1470, 1396, 1306, 1283, 1240, 1011, 881

$^1$H-NMR (CDCl$_3$): δ 10.05 (s, 1H), 8.02 (d, J=8.1 Hz, 1H), 7.21 (d, J=1.7 Hz, 1H), 7.09 (d, J=8.1 Hz, 1H), 4.01 (s, 3H), 2.68 (s, 3H)

$^{13}$C-NMR (CDCl$_3$): δ 187.90, 162.22, 151.19, 139.19, 129.95, 125.48, 115.48, 108.30, 56.38, 10.38

Elemental analysis:
Value calculated for C$_{10}$H$_{10}$N$_4$O$_2$: C, 55.04%; H, 4.62%; N, 25.68%; Value found: C, 54.43%; H, 4.21%; N, 25.29%.

Example 5

2-Methoxy-5-(tetrazol-1-yl)benzaldehyde

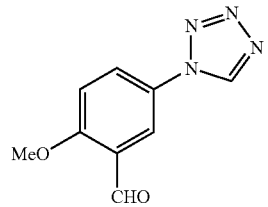

Three grams of 1-(4-methoxyphenyl)-1H-tetrazole (17.0 mmol), 15 ml of methanesulfonic acid, 15 ml of trifluoromethanesulfonic acid, and 4.78 g of hexamethylenetetramine (34.0 mmol) were introduced into a 100 ml flask, and heated to 100° C. for reaction for 3 hours. After reaction, the reaction solution was cooled to room temperature, introduced into 30 ml of water cooled in an ice bath, and stirred at 5° C. for 30 minutes. The reaction solution was then extracted with dichloromethane (60 ml×3), and the organic phase thus obtained was washed with 10% aqueous sodium hydroxide solution (90 ml×1) and water (90 ml×1), and dried over anhydrous magnesium sulfate for 1 hour. After drying, filtration and solvent evaporation were performed, and the crude product thus obtained was subjected to crystallization in a mixed solvent containing 5 ml of dichloromethane and 5 ml of toluene while cooling in an ice bath. After filtration and drying, 1.61 g of 2-methoxy-5-(tetrazol-1-yl)benzaldehyde was obtained as a white solid (yield: 46.3%).

Melting point: 170.7 to 171.7° C.

IR (KBr, cm$^{-1}$): 3125, 1674, 1611, 1506, 1468, 1398, 1281, 1260, 1217, 1186, 1096, 1009, 841

$^1$H-NMR (CDCl$_3$): δ 10.59 (s, 1H), 8.97 (s, 1H), 8.04 (d, J=2.9 Hz, 1H), 7.98 (dd, J=9.0 Hz, 2.9 Hz, 1H), 7.22 (d, J=9.0 Hz, 1H), 4.04 (s, 3H)

Elemental analysis:
Value calculated for C$_9$H$_8$N$_4$O$_2$: C, 52.94%; H, 3.95%; N, 27.44%; Value found: C, 52.69%; H, 3.76%; N, 27.37%.

Example 6

2-Methoxy-5-(5-methyltetrazol-1-yl)benzaldehyde

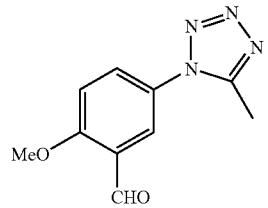

500 mg of 1-(4-methoxyphenyl)-5-methyl-1H-tetrazole (2.63 mmol), 2.5 ml of methanesulfonic acid, 2.5 ml of trifluoromethanesulfonic acid, and 554 mg of hexamethylenetetramine (3.94 mmol) were introduced into a 10 ml flask, and heated to 100° C. for reaction for 2 hours. After reaction, the reaction solution was cooled to room temperature, introduced into 5 ml of water cooled in an ice bath, and stirred at 5° C. for 30 minutes. The reaction solution was then extracted with dichloromethane (10 ml×3), and the organic phase thus obtained was washed with 10% aqueous sodium hydroxide solution (10 ml×1) and water (10 ml×1), and dried over anhydrous magnesium sulfate for 1 hour. After drying, filtration and solvent evaporation were performed, and the crude product thus obtained was purified by column chromatography (silica gel, ethyl acetate:n-hexane=1:1), resulting in 290 mg of 2-methoxy-5-(5-methyltetrazol-1-yl)benzaldehyde as a white solid (yield: 50.6%).

Melting point: 131.9 to 133.5° C.

IR (KBr, cm$^{-1}$): 3010, 2870, 1683, 1616, 1523, 1502, 1393, 1279, 1184, 1018, 843, 633, 536

$^1$H-NMR (CDCl$_3$): δ 10.48 (s, 1H), 7.87 (d, J=2.9 Hz, 1H), 7.69 (d, J=9.0 Hz, 2.9 Hz, 1H), 7.20 (d, J=9.0 Hz, 1H), 4.04 (s, 3H), 2.60 (s, 3H)

$^{13}$C-NMR (CDCl$_3$): δ 187.80, 162.34, 151.52, 131.74, 126.90, 125.19, 124.01, 113.37, 56.39, 9.77

Elemental analysis:
Value calculated for $C_{10}H_{10}N_4O_2$: C, 55.04%; H, 4.62%; N, 25.68%; Value found: C, 55.06%; H, 4.56%; N, 24.97%.

Example 7

2-Methoxy-5-(5-ethyltetrazol-1-yl)benzaldehyde

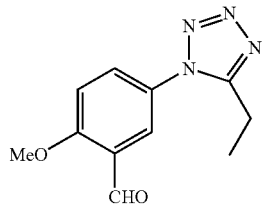

Three grams of 1-(4-methoxyphenyl)-5-ethyl-1H-tetrazole (14.7 mmol), 15 ml of methanesulfonic acid, 15 ml of trifluoromethanesulfonic acid, and 4.13 g of hexamethylenetetramine (29.4 mmol) were introduced into a 100 ml flask, and heated to 100° C. for reaction for 3 hours. After reaction, the reaction solution was cooled to room temperature, introduced into 30 ml of water cooled in an ice bath, and stirred at 5° C. for 30 minutes. The reaction solution was then extracted with dichloromethane (60 ml×3), and the organic phase thus obtained was washed with 10% aqueous sodium hydroxide solution (90 ml×1) and water (90 ml×1), and dried over anhydrous magnesium sulfate for 1 hour. After drying, filtration and solvent evaporation were performed, and the crude product thus obtained was subjected to crystallization in a mixed solvent containing 3 ml of dichloromethane and 12 ml of isopropyl alcohol while cooling in an ice bath. After filtration and drying, 1.28 g of 2-methoxy-5-(5-ethyltetrazol-1-yl)benzaldehyde was obtained as a white solid (yield: 37.5%). Melting point: 137.5 to 138.4° C.

IR (KBr, cm$^{-1}$): 1682, 1612, 1501, 1452, 1396, 1279, 1246, 1182, 1173, 1117, 1055, 1015, 843, 652, 534

$^1$H-NMR (CDCl$_3$): δ 10.49 (s, 1H), 7.85 (d, J=2.7 Hz, 1H), 7.66 (dd, J=9.0 Hz, 2.7 Hz, 1H), 7.19 (d, J=9.0 Hz, 1H), 4.04 (s, 3H), 2.88 (q, J=7.6 Hz, 2H), 1.37 (t, J=7.6 Hz, 3H)

$^{13}$C-NMR (CDCl$_3$): δ 187.54, 162.19, 155.86, 131.81, 126.59, 124.97, 124.16, 113.31, 56.36, 17.41, 11.51

Elemental analysis:
Value calculated for $C_{11}H_{12}N_4O_2$: C, 56.89%; H, 5.21%; N, 24.12%; Value found: C, 56.58%; H, 5.26%; N, 24.11%.

Example 8

2-Methoxy-5-(5-trifluoromethyltetrazol-1-yl)benzaldehyde

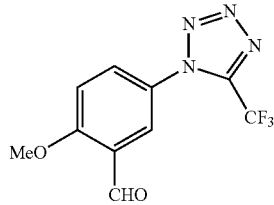

Two grams of 1-(4-methoxyphenyl)-5-trifluoromethyl-1H-tetrazole (8.19 mmol), 20 ml of methanesulfonic acid, and 1.38 g of hexamethylenetetramine (9.83 mmol) were introduced into a 50 ml flask, and heated to 100° C. for reaction for 3 hours. After reaction, the reaction solution was cooled to room temperature. 20 ml of water cooled in an ice bath was added to the reaction solution, and the reaction solution was then stirred at 5° C. for 30 minutes. The reaction solution was then extracted with toluene (20 ml×2), and the organic phase thus obtained was washed with 10% aqueous sodium hydroxide solution (20 ml×1) and water (20 ml×1), and dried over anhydrous magnesium sulfate for 1 hour. After drying, filtration and solvent evaporation were performed, and the crude product thus obtained was purified by column chromatography (silica gel, ethyl acetate:n-hexane=1:1), resulting in 0.61 g of 2-methoxy-5-(5-trifluoromethyltetrazol-1-yl)benzaldehyde as a white solid (yield: 27.4%).

Melting point: 117.0 to 117.3° C.

IR (KBr, cm$^{-1}$): 1684, 1612, 1533, 1499, 1456, 1396, 1319, 1283, 1250, 1205, 1161, 1109, 1051, 1034, 1016, 839, 652

$^1$H-NMR (CDCl$_3$): δ 9.95 (s, 1H), 8.15 (dd, J=8.5 Hz, 2.0 Hz, 1H), 7.94 (d, J=2.0 Hz, 1H), 7.25 (d, J=8.5 Hz, 1H), 3.92 (s, 3H) $^{13}$C-NMR (CDCl$_3$): δ 187.21, 163.08, 146.62, 146.19, 145.78, 145.36, 131.85, 125.34, 125.19, 125.16, 121.71, 119.01, 116.31, 113.61, 113.25, 56.52

Elemental analysis:
Value calculated for $C_{10}H_7F_3N_4O_2$: C, 44.13%; H, 2.59%; N, 20.58%; Value found: C, 44.43%; H, 2.59%; N, 20.53%.

Example 9

2-Methoxy-5-(5-trifluoromethyltetrazol-1-yl)benzaldehyde

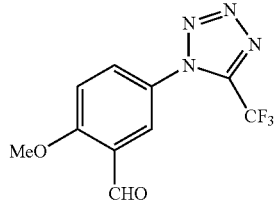

Fifteen grams of 1-(4-methoxyphenyl)-5-trifluoromethyl-1H-tetrazole (61.4 mmol), 37.5 ml of methanesulfonic acid, 37.5 ml of trifluoromethanesulfonic acid, and 17.22 g of hexamethylenetetramine (122.8 mmol) were introduced into a 300 ml flask, and heated to 100° C. for reaction for 2 hours. After reaction, the reaction solution was cooled to room temperature, introduced into 75 ml of water cooled in an ice bath, and stirred at 5° C. for 30 minutes. The reaction solution was then extracted with chloroform (150 ml×2), and the organic phase thus obtained was washed with 10% aqueous sodium hydroxide solution (150 ml×1) and water (150 ml×1), and dried over anhydrous magnesium sulfate for 1 hour. After drying, filtration and solvent evaporation were performed, and the crude product thus obtained was subjected to crystallization in 75 ml of isopropyl alcohol while cooling in an ice bath. After filtration and drying, 11.66 g of 2-methoxy-5-(5-trifluoromethyltetrazol-1-yl)benzaldehyde was obtained as a white solid (yield: 69.7%).

Melting point: 117.0 to 117.3° C.

IR (KBr, cm$^{-1}$): 1684, 1612, 1533, 1499, 1456, 1396, 1319, 1283, 1250, 1205, 1161, 1109, 1051, 1034, 1016, 839, 652

$^1$H-NMR (CDCl$_3$): δ 9.95 (s, 1H), 8.15 (dd, J=8.5 Hz, 2.0 Hz, 1H), 7.94 (d, J=2.0 Hz, 1H), 7.25 (d, J=8.5 Hz, 1H), 3.92 (s, 3H) $^{13}$C-NMR (CDCl$_3$): δ 187.21, 163.08, 146.62, 146.19, 145.78, 145.36, 131.85, 125.34, 125.19, 125.16, 121.71, 119.01, 116.31, 113.61, 113.25, 56.52

Elemental analysis:

Value calculated for C$_{10}$H$_7$F$_3$N$_4$O$_2$: C, 44.13%; H, 2.59%; N, 20.58%; Value found: C, 44.43%; H, 2.59%; N, 20.53%.

Example 10

2-Ethoxy-5-(5-trifluoromethyltetrazol-1-yl)benzaldehyde

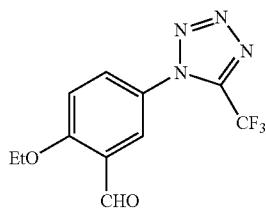

Four grams of 1-(4-ethoxyphenyl)-5-trifluoromethyl-1H-tetrazole (15.5 mmol), 10 ml of methanesulfonic acid, 10 ml of trifluoromethanesulfonic acid, and 4.34 g of hexamethylenetetramine (31.0 mmol) were introduced into a 100 ml flask, and heated to 100° C. for reaction for 2 hours. After reaction, the reaction solution was cooled to room temperature, introduced into 20 ml of water cooled in an ice bath, and stirred at 5° C. for 30 minutes. The reaction solution was then extracted with chloroform (50 ml×3), and the organic phase thus obtained was washed with 10% aqueous sodium hydroxide solution (80 ml×1) and water (80 ml×1), and dried over anhydrous magnesium sulfate for 1 hour. After drying, filtration and solvent evaporation were performed, and the crude product thus obtained was purified by column chromatography (silica gel, chloroform), resulting in 1.01 g of 2-ethoxy-5-(5-trifluoromethyltetrazol-1-yl)benzaldehyde as a white solid (yield: 22.8%).

Melting point: 87.9 to 88.4° C.

IR (KBr, cm$^{-1}$): 3075, 2941, 2889, 1692, 1609, 1533, 1501, 1447, 1389, 1321, 1285, 1271, 1246, 1211, 1171, 1155, 1118, 1038, 816, 669

$^1$H-NMR (CDCl$_3$): δ 10.51 (s, 1H), 7.94 (d, J=2.7 Hz, 1H), 7.66 (dd, J=8.8 Hz, 2.7 Hz, 1H), 7.23 (d, J=8.8 Hz, 1H), 4.30 (q, J=7.0 Hz, 2H), 1.57 (d, J=7.0 Hz, 3H)

$^{13}$C-NMR (CDCl$_3$): δ 187.66, 162.81, 146.79, 146.39, 145.97, 145.55, 131.91, 125.24, 121.84, 119.14, 116.44, 113.97, 113.73, 65.25, 14.43

Elemental analysis:

Value calculated for C$_{11}$H$_9$F$_3$N$_4$O$_2$: C, 46.16%; H, 3.17%; N, 19.58%; Value found: C, 45.99%; H, 3.05%; N, 20.08%.

The invention claimed is:

1. A process for producing an alkoxy-(tetrazol-1-yl)benzaldehyde compound represented by Formula (2):

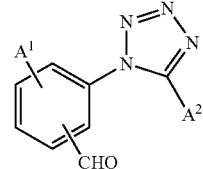

(2)

wherein A$^1$ is an alkoxy group, and A$^2$ is a hydrogen atom, alkyl group or fluorine-substituted alkyl group, the process comprising reacting a 1-(alkoxyphenyl)-1H-tetrazole compound represented by Formula (1):

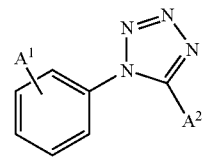

(1)

wherein A$^1$ and A$^2$ are as defined above, with hexamethylenetetramine in a sulfonic acid' solvent, followed by hydrolysis.

2. The process according to claim 1, wherein the sulfonic acid solvent is a mixed solvent of methanesulfonic acid and trifluoromethanesulfonic acid.

3. The process according to claim 1, wherein hexamethylenetetramine is used in an amount of 1.0 to 3.0 mol per mol of the 1-(alkoxyphenyl)-1H-tetrazole compound.

4. The process according to claim 1, wherein A$^1$ is a methoxy group, and A$^2$ is a hydrogen atom, methyl group, ethyl group or trifluoromethyl group.

5. A process for producing a 4-alkoxy-3-(tetrazol-1-yl)benzaldehyde compound represented by Formula (4):

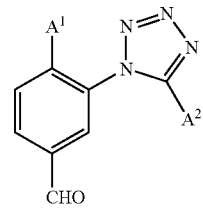

(4)

wherein A$^1$ is an alkoxy group, and A$^2$ is a hydrogen atom, alkyl group or fluorine-substituted alkyl group, the process comprising reacting a 1-(2-alkoxyphenyl)-1H-tetrazole compound represented by Formula (3):

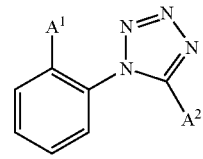

(3)

wherein $A^1$ and $A^2$ are as defined above, with hexamethylenetetramine in a sulfonic acid solvent, followed by hydrolysis.

6. A process for producing a 2-alkoxy-4-(tetrazol-1-yl) benzaldehyde compound represented by Formula (6):

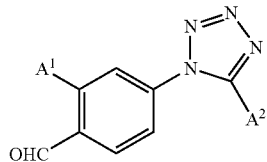

(6)

wherein $A^1$ is an alkoxy group, and $A^2$ is a hydrogen atom, alkyl group or fluorine-substituted alkyl group, the process comprising reacting a 1-(3-alkoxyphenyl)-1H-tetrazole compound represented by Formula (5):

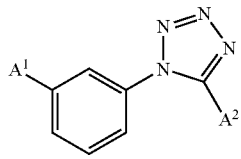

(5)

wherein $A^1$ and $A^2$ are as defined above, with hexamethylenetetramine in a sulfonic acid solvent, followed by hydrolysis.

7. A process for producing a 2-alkoxy-5-(tetrazol-1-yl) benzaldehyde compound represented by Formula (8):

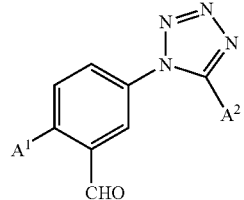

(8)

wherein $A^1$ is an alkoxy group, and $A^2$ is a hydrogen atom, alkyl group or fluorine-substituted alkyl group, the process comprising reacting a 1-(4-alkoxyphenyl)-1H-tetrazole compound represented by Formula (7):

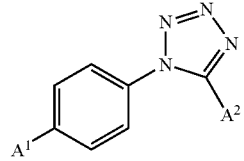

(7)

wherein $A^1$ and $A^2$ are as defined above, with hexamethylenetetramine in a sulfonic acid solvent, followed by hydrolysis.

* * * * *